(12) United States Patent  (10) Patent No.: US 8,951,252 B2
Steiner et al.  (45) Date of Patent: *Feb. 10, 2015

(54) EXTERNAL FIXATION SYSTEM (75) Inventors: Christian Steiner, Eisenach (DE);
Vinzenz Burgherr, Bern (CH);
Meinrad Fiechter, Münsingen (CH)

(73) Assignee: Stryker Trauma SA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/115,479

(22) Filed: May 25, 2011

(65) Prior Publication Data

US 2011/0288549 A1 Nov. 24, 2011

Related U.S. Application Data

(63) Continuation of application No. 12/157,612, filed on Jun. 11, 2008, now Pat. No. 7,955,334.

(30) Foreign Application Priority Data

Apr. 18, 2008 (EP) .................................... 08154754

(51) Int. Cl.
*A61B 17/62* (2006.01)

(52) U.S. Cl.
CPC ..................................... *A61B 17/62* (2013.01)
USPC .......................................................... 606/56

(58) Field of Classification Search
USPC .......... 606/53–59, 280, 70, 71, 281, 283–285
See application file for complete search history.

(56) References Cited

U.S. PATENT DOCUMENTS

| 2,055,024 | A | 9/1936 | Bittner |
| 3,863,037 | A | 1/1975 | Schindler et al. |
| 4,006,740 | A | 2/1977 | Volkov et al. |
| 4,098,269 | A | 7/1978 | Judet |

(Continued)

FOREIGN PATENT DOCUMENTS

| DE | 4421223 | 12/1995 |
| FR | 2576774 A1 | 8/1986 |

(Continued)

OTHER PUBLICATIONS

European Search Report, EP 08 15 7614.

(Continued)

*Primary Examiner* — Jerry Cumberledge
*Assistant Examiner* — Nicholas Plionis
(74) *Attorney, Agent, or Firm* — Lerner, David, Littenberg, Krumholz & Mentlik, LLP (57) ABSTRACT

An orthopedic fixation ring for an external fixator has a ring or a ring-segment extending around a center axis. The ring comprises a first surface running perpendicular to the center axis, a second surface which is parallel to the first surface, and a plurality of spaced apart through openings running parallel to the center axis and extending through the fixation plate. The fixation plate has at least a third surface which is parallel to the first surface spaced outwardly thereof with respect to the center axis. A further set of through openings extends from the first surface to the third surface. A fourth surface may be provided which is axially displaced from the second surface with respect to the center axis. The ring preferably is circular or part-circular and is molded from carbon fiber reinforced PEEK.

16 Claims, 6 Drawing Sheets

(56) References Cited

U.S. PATENT DOCUMENTS

| | | |
|---|---|---|
| 4,185,623 A | 1/1980 | Volkov et al. |
| 4,308,863 A | 1/1982 | Fischer |
| 4,365,624 A | 12/1982 | Jaquet et al. |
| 4,403,606 A | 9/1983 | Woo et al. |
| 4,450,834 A | 5/1984 | Fischer |
| 4,784,125 A | 11/1988 | Monticelli et al. |
| 4,889,111 A | 12/1989 | Ben-Dov |
| 5,062,844 A | 11/1991 | Jamison et al. |
| 5,087,258 A | 2/1992 | Schewior |
| 5,496,319 A | 3/1996 | Allard et al. |
| 5,702,389 A | 12/1997 | Taylor et al. |
| 5,722,976 A | 3/1998 | Brown |
| 5,728,095 A | 3/1998 | Taylor et al. |
| 5,779,703 A | 7/1998 | Benoist |
| 5,891,143 A | 4/1999 | Taylor et al. |
| 5,968,043 A | 10/1999 | Ross, Jr. et al. |
| 5,971,984 A | 10/1999 | Taylor et al. |
| 5,997,537 A | 12/1999 | Walulik |
| 6,030,386 A | 2/2000 | Taylor et al. |
| 6,391,250 B1 | 5/2002 | Wolfsgruber et al. |
| 7,226,449 B2 | 6/2007 | Venturini et al. |
| RE40,914 E | 9/2009 | Taylor et al. |
| 8,257,353 B2 | 9/2012 | Wong et al. |
| 2004/0073212 A1 | 4/2004 | Kim |
| 2004/0133203 A1* | 7/2004 | Young et al. .................... 606/61 |
| 2004/0167518 A1 | 8/2004 | Estrada, Jr. |
| 2007/0049930 A1 | 3/2007 | Hearn et al. |
| 2008/0221571 A1 | 9/2008 | Daluiski et al. |

FOREIGN PATENT DOCUMENTS

| | | |
|---|---|---|
| RU | 2211000 | 8/2003 |
| WO | 92/14426 | 9/1992 |
| WO | 97/30650 | 8/1997 |
| WO | 97/30651 | 8/1997 |
| WO | 01/22892 | 4/2001 |
| WO | 2007075114 | 7/2007 |

OTHER PUBLICATIONS

European Search Report, EP 08 15 4754.

Nanua et al., IEEE Transactions on Robotics and Automation, vol. 6, No. 4, pp. 438-444, Aug. 1990.

* cited by examiner

FIG. 12

EXTERNAL FIXATION SYSTEM

CROSS-REFERENCE TO RELATED APPLICATIONS

This application is a continuation of U.S. application Ser. No. 12/157,612, filed on Jun. 11, 2008 now U.S. Pat. No. 7,955,334, which claims priority of European Application No. 08 154 754.9 Filed on Apr. 18, 2008, the disclosures of which are incorporated herein by reference.

BACKGROUND OF THE INVENTION

External orthopedic fixation systems having the shape of plates or rings for the use with clamps and bone are known for fracture fixation. The person skilled in the art knows such rings for example from the Illizarov Apparatus. Thereby several rings are positioned around limbs interconnected by struts and used to accommodate elements such as posts etc. which are in connection with a Kirchner wire or pin connected to a bony structure on either side of a fracture. Such rings are commonly used for wire placement or pin placement. Tensioned wires are in an engagement with said bony structure and at two circumferentially spaced positions on a single ring.

U.S. Pat. No. 5,275,598, for example, discloses a ring having several openings that are arranged in regular intervals. Thereby the wires are fixed by means of nuts and bolts with the opening of the ring. Several wires are arranged such that they extend from one side of the ring across the inner ring diameter to the other side of the ring. Consequently, the wires cross at a certain location. If the wires lie more or less in the same plane the wires have to be bent so that they avoid interference with one another. Upon tensioning of this distorted wire, an unstable force occurs at the intersection. This instability leads to bone movements and can disorient the fracture.

Some prior art devices use wire clamps which can be shifted in height in order to arrange several wires extending in several parallel planes. The use of different wire clamps is cumbersome and complicated for the medical practitioner as the height of said clamps has to be adjusted for example, to provide the separate parallel planes for each wire.

Furthermore the person skilled in the art alternatively uses a plurality of washers together with bolts and nuts in order to place wires in different planes. However, the use of such elements is rather cumbersome and complicated. Furthermore the use of bolts and nuts requires that the medical practitioner has to use two wrenches or other tools in order to tighten the bolts and the nuts.

SUMMARY OF THE INVENTION

One aspect of the present invention is to provide an external orthopedic fixation ring for use with an external fixator that overcomes the disadvantages of prior art fixation rings. In particular the fixation ring shall be shaped to allow a simple placement of wires or pins in different planes or levels.

An external orthopedic fixation ring for an external fixator having the shape of a complete ring or a ring-segment extending essentially around a center axis comprises a first surface running perpendicular to said centre axis, a second surface which is parallel to the first surface, and a plurality of spaced apart through openings having central axes running parallel to the center axis of the ring and extending through the fixation plate. The fixation plate comprises at least a third surface which is parallel to the first. A further set of through openings extends from the first surface to the third surface. The third surface is axially spaced from the first and second surfaces in the direction of the central axis.

The first, second and third surfaces provide three parallel and displaced planes in each of which a wire can be arranged. This is particularly advantageous as the wires cross themselves in different planes. This prevents a bending of the wires in the vicinity of the crossing point.

Preferably the fixation ring comprises a fourth surface which is parallel to the first surface. A set of through openings extends from the second surface to the fourth surface. The fourth surface is again spaced along the central ring axis from the other surfaces.

Preferably the third surface is provided by a first embossment or a set of embossments around the ring circumference that is/are arranged on the second surface.

Preferably the fourth surface is provided by means of a second embossment or a set of embossments that is/are arranged on the first surface.

Preferably a plurality of spaced apart first embossments are arranged in regular intervals distributed over the respective surface and/or a plurality of spaced apart second embossments are arranged in regular intervals distributed over the respective surface.

Preferably the first embossments and/or the second embossments are arranged such that one embossment is/are allocated to every second through opening. Preferably the first embossments are allocated to every even numbered through opening and the second embossments to every odd numbered opening.

Preferably the edges of the embossments are tapered towards the openings such that the clearance between two neighboring embossments decreases towards the opening and increases from the opening as viewed in radial direction from the centre axis of the ring. Thus in one embodiment the spaces between embossments widen on moving from the openings towards the inner ring circumference.

Preferably the plate comprises at least two ring segments which ring segments are connected by means of screws.

The rings are preferably molded from a radiolucent polymeric material such as carbon fiber reinforced poly ether ether Ketone (PEEK).

An external fixation system providing the above aspects of the invention comprises a support ring or a ring-segment extending around a central axis (M). The ring or segment has a first surface extending perpendicular to central axis (M), a second surface which is parallel to the first surface, and a plurality of spaced apart through openings running parallel to the center axis (M) extending through the ring from the first to the second surface. A third surface is provided which is parallel to the first and second surfaces with a plurality of through openings running parallel to axis (M) extending from the first surface to the third surface and wherein the first, second and third surfaces are axially spaced apart with respect to the central axis (M) from the other surfaces. The support or ring segment preferably comprises a fourth surface which extends parallel to the first, second and third surfaces.

A plurality of through openings extend from the second surface to the fourth surface and wherein the fourth surface is spaced with respect to the central axis (M) from the first, second and third surfaces. The third surface is preferably formed by a plurality of first circumferentially spaced embodiments on the second surface. The fourth surface is preferably formed by a plurality of circumferentially spaced embodiments on the first surface. The plurality of spaced apart first embossments can be spaced at regular intervals over the second surface and the plurality of spaced apart second embossments can be spaced at regular intervals distributed over the first surface. The first and second embossment can be connected by a means of a web with a neighboring embossment. The first and second embossments may be arranged such that of the first and second embossments alternate around adjacent through openings around the ring. The first embossments are preferably allocated to every even-numbered through opening of a multiplicity of through openings and the second embodiments are allocated to odd numbered through opening of the multiplicity of through openings. The edges of the embossments may be tapered towards the openings such that a clearance between two neighboring embossments decreases towards the opening and increases from away the openings as viewed in radial direction from the center axis (M).

The external fixation system may comprise at least two ring segments which ring segments are connected by means of screws. The preferred screws have an axial bore along the middle axis of the screw. Other aspects of the invention are provided by an external fixation system having a circular or part circular ring having first and second parallel planar surfaces with a multiplicity of openings extending therethrough and first and second embossments surrounding the openings. The first embossment extend away from the first ring surface and the second embossment extend away from the second surface. The first and second embossments alternate with respect to adjacent openings. The first and second embossments define third and fourth planar surfaces each parallel to the first and second surfaces. The first embossment and a second embossment are connected by a means of a web with a neighboring embossment. The edges of the embossments are preferably tapered towards the openings such that a clearance between two neighboring embossments decreases towards the opening and increases from away the opening as viewed in radial direction from the center axis (M). The ring may comprise at least two ring segments which ring segments are connected by screws. The connecting screws have an axial bore along the central longitudinal axis of the screw.

BRIEF DESCRIPTION OF THE DRAWINGS

The drawings will be explained in greater detail by means of a description of an exemplary embodiment, with reference to the following figures.

DETAILED DESCRIPTION

Figure 1:
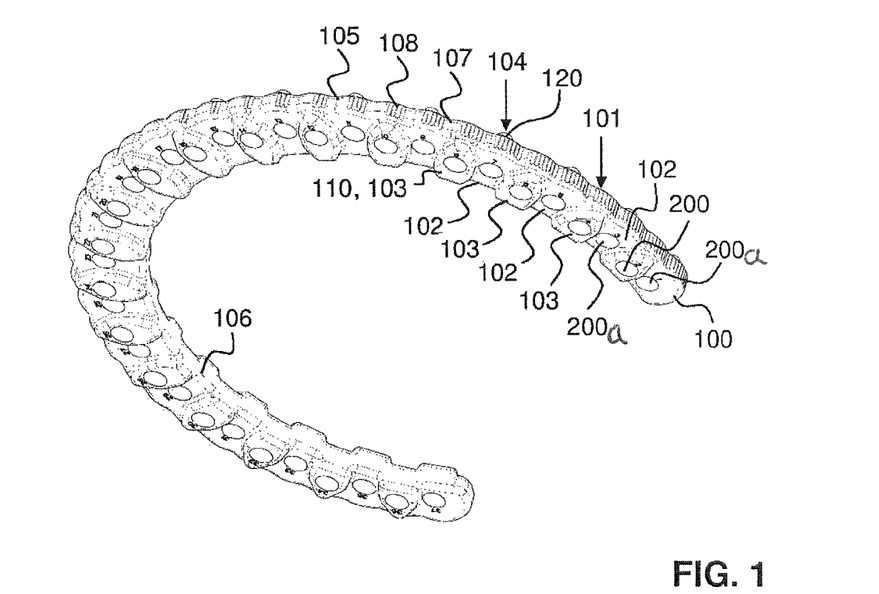
FIG. 1 shows a perspective view of a first embodiment of an external fixation ring according to the present invention.
Figure 2:
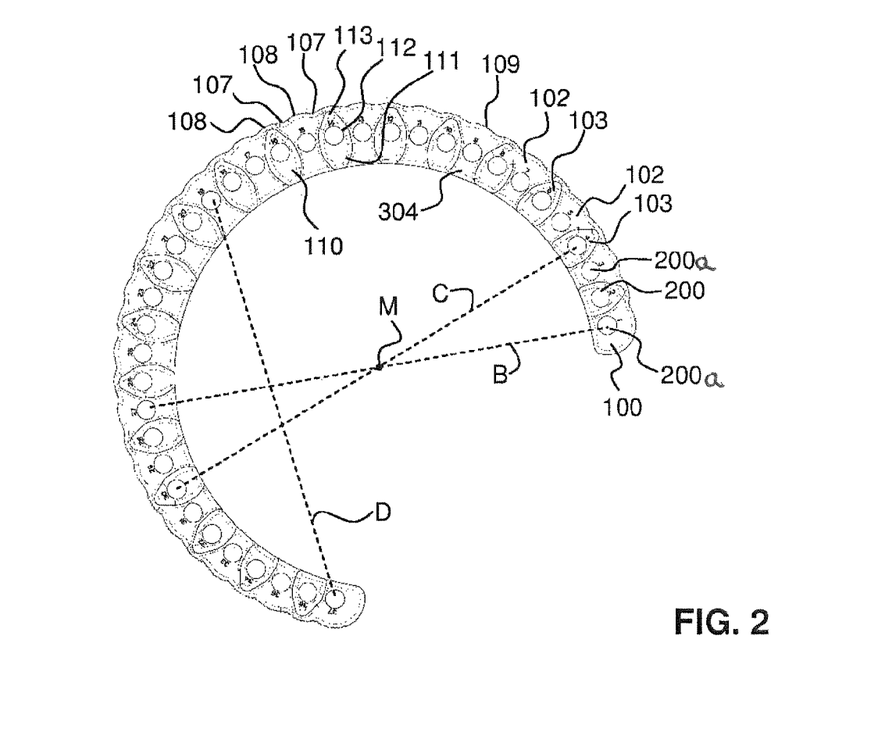
FIG. 2 shows a bottom view of the first embodiment shown in FIG. 1.
Figure 3:
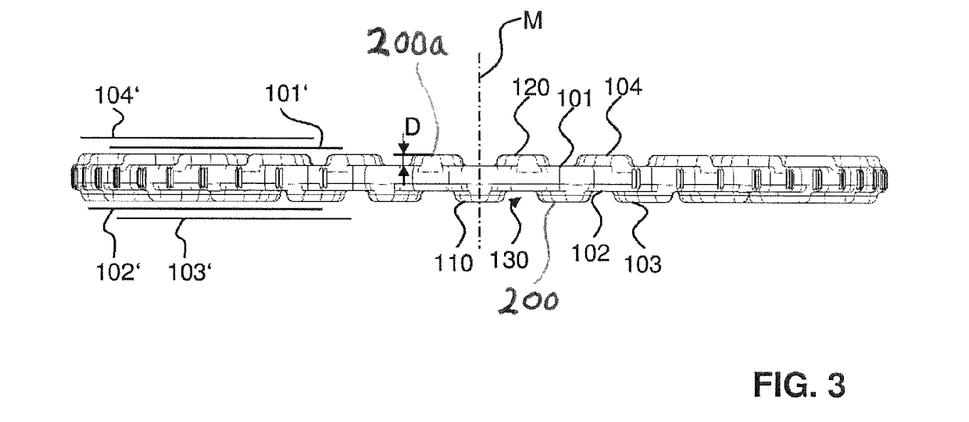
FIG. 3 shows a front view of the first embodiment shown in FIG. 1.

Referring to FIGS. 1 to 3 there is shown an external fixation system generally denoted as 10 according to a first embodiment of the present invention comprising an open ring segment. The orthopedic fixation plate is used to accommodate clamped elements in order to fixate a wire (e.g. a Kuentscher Wire) or pin that is in an engagement with a bony structure such as a fractured long bone to the ring. In the preferred embodiment the external fixation plate has the shape of a ring segment covering an angle at about 250° to 260°.

The preferred fixation ring 100 has the shape of a circular ring or of a ring segment having a central axis (M) around which the ring extends. The ring 100 comprises a first surface 101 and a second surface 102. The first surface 101 and the second surface 102 are parallel to each other and both are perpendicular to the central ring (M). The ring is furthermore limited by an outer surface 105 and an inner surface 106.

The fixation plate 100 comprises furthermore a plurality of two sets of through openings or bores 200, 200a extending parallel to the central axis (M) through the fixation plate 100. The bores of each set 200, 200a alternate around the ring 100 or ring segment. The through openings 200, 200a are able to accommodate an element such as a clamping element in order to fixate a preferably tensioned wire extending through a limb of a human body to the fixation plate 100. Therefore the openings of sets 200 or 200a have a corresponding cross-section to the element. In the present embodiment, the openings of sets 200, 200a are designed as circular openings but any other shapes such as rectangular, quadratic, polygonal or elliptical may also be used. The wire or pin mounting element may be a wire post or a bolt and a nut. The openings of sets 200, 200a are arranged in regular spaced intervals, preferably evenly distributed over the circumference of the whole plate 100. In the preferred embodiment the openings of sets 200, 200a are distributed along a circle having the same central axis as the fixation plate 100. The diameter of the circle is between the diameter of the outer surface 105 and of the inner surface 106, preferably the circle lies equivalent from the diameters 105 and 106. Alternatively the openings of sets 200, 200a can also be arranged such that each bore opening is arranged on a different radius or circle. This means that the distance from the opening of sets 200, 200a to the center of the ring or ring segment is different or non-constant for each opening in the sets 200, 200a.

The preferred ring 100 or fixation plate further comprises at least a third surface 103 which is substantially parallel to the first surface 101 and the second surface 102. The third surface 103 is spaced along the central axis (M) from the first surface 101 as well as from the second surface 102 in the axial direction. The third surface 103 here is provided by first embossments 110 which are arranged on the second surface 102. The first embossments 110 extend axially generally perpendicular to the first surface 101 as well as second surface 102 and terminate in direction of the central axis in the third surface 103. This means that the fixation plate comprises three surfaces 101, 102, 103 which are at different levels or axially displaced in direction of the central axis (M) from each other. Referring to FIG. three a first set of through openings 200 are arranged such that they extend from the second surface 102 through the plate 100 to the third surface 103. The second set of through openings 200a are arranged such that they extend from the first surface 101 to the second surface 102 (there being no second embossment in this embodiment).

Furthermore the preferred ring 100 shown in FIGS. 1 to 3 comprises a fourth surface 104 which is also substantially parallel to the first surface 101 and the second surface 102. As with the third surface 103, the fourth surface 104 is axially spaced with respect to axis from the other surfaces 101, 102, 103. The fourth surface 104 is provided by second embossments 120 which are arranged on the first surface 101. Thereby the second embossments 120 extend away from and generally perpendicular to the second surface 102 and terminate in fourth surface 104. This means that the ring comprises four surfaces 101, 102, 103, 104 which are at four different levels which are shifted with respect of axis M i.e. spaced axially in direction of the central axis M with respect to each other. These surfaces may be parallel. The set of through openings 200*a* are arranged such that they extend from the first surface 101 through the plate 100 to the fourth surface 104. A further set of through openings 200 extend from the second surface 102 through the plate 100 to third surface 103.

As with the openings 200, 200*a* the embossments 110, 120 are also arranged in regular spaced alternating intervals evenly distributed around the entire ring 100. With respect to the openings 200 the first embossments 110 are arranged such that for every even-numbered opening 2, 4, 6, etc. one first embossment 110 is provided, whereas the second embossments 120 including bores 200*a* are arranged such that for every odd numbered opening 1, 3, 5, etc. one second embossment 120 is provided. Thus in the preferred embodiment the first and second embossments alternate around the ring circumference. This results in a structure where every first surface 101 is followed by a fourth surface 104 and where every second surface 102 is followed by third surface 103. Therefore an alternating up-and-down structure is provided on the first surface 101 and/or on the second surface 102 of the fixation plate 100.

In the preferred embodiment the first embossment 110 and the second embossment 120 are arranged angularly shifted as viewed from the center axis (M). In other words: in a certain angular segment in which a first embossment 110 is arranged no second embossment 120 is arranged and vice-versa. In other embodiments (not shown) it may be possible that the first embossment 110 and the second embossment 120 are allocated to the same openings of sets 200 and 200*a*, i.e. always to the even-numbered opening or to the odd-numbered opening, respectively. Thus two levels with the maximum wire spacing followed by two levels with the minimum spacing may be provided.

One can also see that the third surface 103 or the fourth surface 104 of the plate 100 comprises several recesses 130 which are evenly distributed over the whole plate 100. Thereby the recesses 130 extend parallel to the central axis M into the plate and provide the first surface 101 and the second surface 102.

Several wires can be fixed by means of the above mentioned elements to the ring 100 via the bores or openings in sets 200, 200*a*. Thereby similar fixation elements (e.g. a wire post or nuts and bolts) are used for every connection point. Due to the use of similar elements the distance between the respective surfaces 101-104 and the axis of the wire is for each wire the same. The wires cross themselves therefore in different planes or levels which prevents bending the wires at the crossing points of the wire. Generally speaking the wires extend in planes which are parallel to the respective surfaces 101-104 wherein each of the planes has the same distance to the wire. The four planes are schematically shown in FIG. 3 with the reference numerals 101'-104'.

Broken lines B and C in FIG. 2 illustrate such wires. Wire B runs from opening 1 to opening 27 whereas wire C runs from opening 4 to opening 30. The crossing point in that example is also the center M' through which the central axis M of the ring runs. It is important to note that the wires extend generally in a plane being parallel to the surfaces 101-104.

FIG. 2 shows also the shape of the embossments 120. The embossment 120 comprises three sections, namely a first section 111, a middle section 112 and a second section 113. The first section 111 is located towards the central axis of the ring whereas the second section 113 is arranged towards the outer side of the ring. The openings in set 200*a* extend preferably through the middle section 112. Depending on the location on the ring, the first section 111 is preferably designed such that its cross-sectional surface as viewed tangential to the ring diminishes towards the center such that the clearance between an embossment 110 and its neighboring embossment 110 increases towards the center. The increasing clearance is necessary, if the medical practitioner wants to place a wire in an angle that is close to the tangent of the ring. Such a wire is illustrated by means of broken line D. The same features as just described apply also for the first embossment 110.

As can be seen from FIGS. 1 and 2 the plate 100 comprises several rounded or concave recesses 107. Recesses 107 extend from outer surface 105 into the ring 100. The center axis of the rounding of the rounded recess 107 runs parallel to the center axis M of the plate 100. Preferably the recesses 107 are arranged such that they extend into the plate 100 between two adjacent openings of sets 200, 200*a*. The crossover 108 from one recess 107 to another neighboring recess 107 is also rounded, here in a convex manner. This means that the outer surface 105 is more or less shaped as wave-like structure. Some of the recesses 107 comprises further a plurality of grooves 109 extending from the recess 107 into the plate 100.

Figure 11:
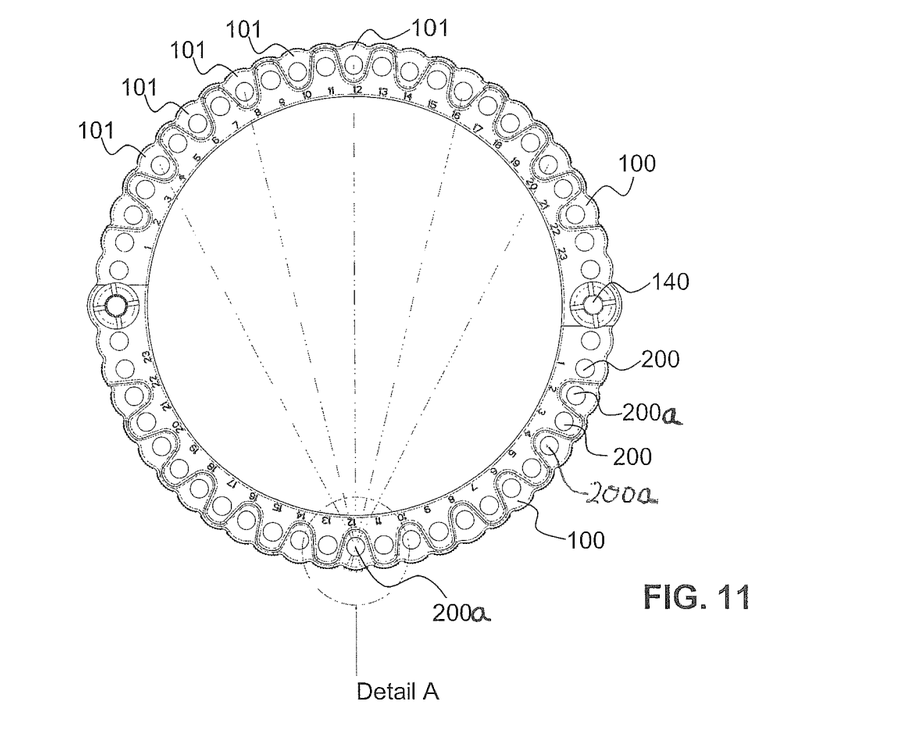
FIG. 11 shows a top view of a complete ring of the invention.
Figure 12:
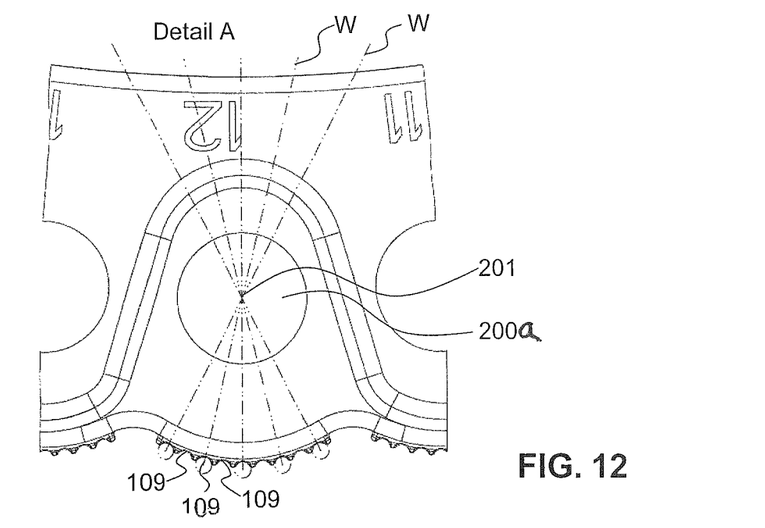
FIG. 12 shows an enlarged view of a through hole of detail A of FIG. 11.

The grooves 109 are arranged in order to orient a wire. With reference to FIGS. 11 and 12 several possible alignments of a wire W to ring 100 are shown with broken lines. Thereby the wires extend from a center point of a groove 109 through the center point 201 of the opening of sets 200, 200*a* to a corresponding opening of sets 200, 200*a* on the other side of the ring or ring-segment. The grooves 109 are arranged such that the wires run to the corresponding opening of sets 200, 200*a* on the other side of the ring 100 (thus having the same level). This is illustrated in FIG. 11. The opening of set 200*a* having the number 12 serves as the origin opening of set 200*a*. It can be seen that the wire may be connected to any other opening of set 200*a* on the other side. In the embodiment shown, the lines W run from opening 12 to openings 4, 8, 12, 16 and 20. In FIG. 12 this situation is shown in detail. Thereby it can be seen that the lines W run here from every second groove 109 which explains that in FIG. 11 the lines W extend from opening 12 to every second even-numbered opening. The medical practitioner may use an alignment apparatus in order to align the wires properly. Thereby the alignment apparatus is oriented to the opening of set 200*a* and to the grooves 109 in order to focus on the corresponding openings on the other side of the ring or ring-segment.

Figure 4:
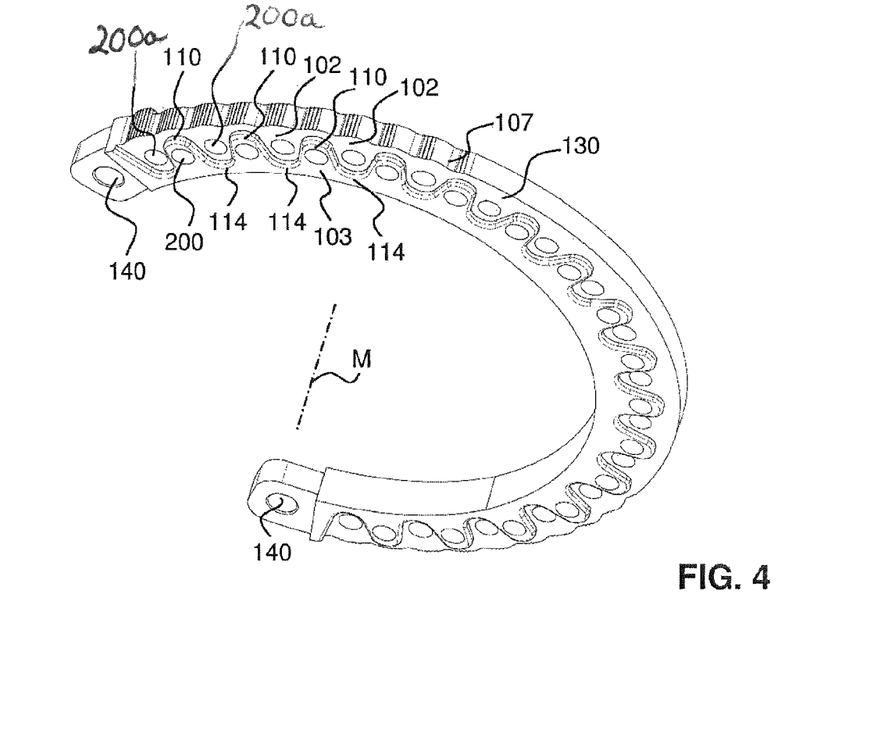
FIG. 4 shows a perspective view of a second embodiment of an external fixation ring according to the present invention.
Figure 5:
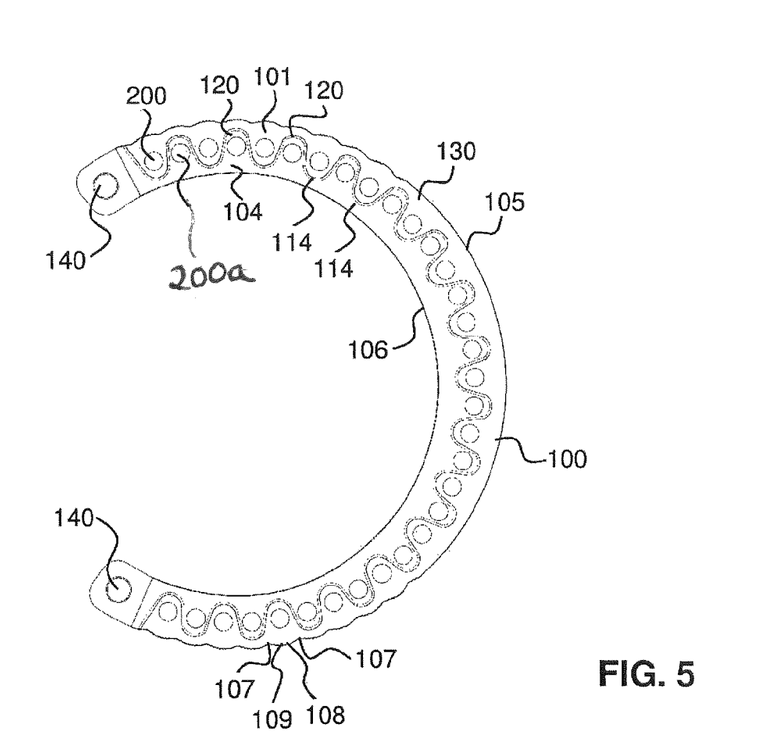
FIG. 5 shows a top view of the second embodiment shown in FIG. 2.

FIGS. 4 and 5 show a further embodiment according to the present invention. In this embodiment the first embossments 110 are connected to each other by means of a web 114. Web 114 extends from one embossment 110 to another neighboring embossment 110 on the inner side 106 of the ring which is closer to the central axis M. In other words, the first embossments 110 are provided by means of recesses 130 that are arranged within the plate 100. The base of the recess provides the first surface 101 and the surface of the embossment is the second surface. The above description for the first embossment applies also for the second embossment 120 on the opposite side of the ring. The connection of the embossments (e.g. by means of web 114) enhances the stiffness and stability of the ring or ring segment.

The external fixator according to FIGS. 4 and 5 is also shaped as a ring-segment. Each of the end portions of the ring comprises one opening 140. Openings 140 serve as a connection opening in order to connect the ring segment as shown with a second ring segment such that a complete ring can be provided. Thereby a screw as is described with regard to FIGS. 7 and 8 may be used. Note that in the vicinity of opening 140 recesses 109 may be omitted in order to obtain a stiffer structure.

Furthermore the plate according to FIGS. 4 and 5 comprises also recesses 107 that are arranged in the outer surface 105 of the plate 100. In that embodiment the recesses 107 are arranged such that they extend only over certain angular segments of the outer surface 105, i.e. not over the whole outer surface 105. In the embodiment shown, recesses 107 are arranged in the areas close to the openings 140 to serve as index points for angling the connection element holding the wire.

Figure 6:
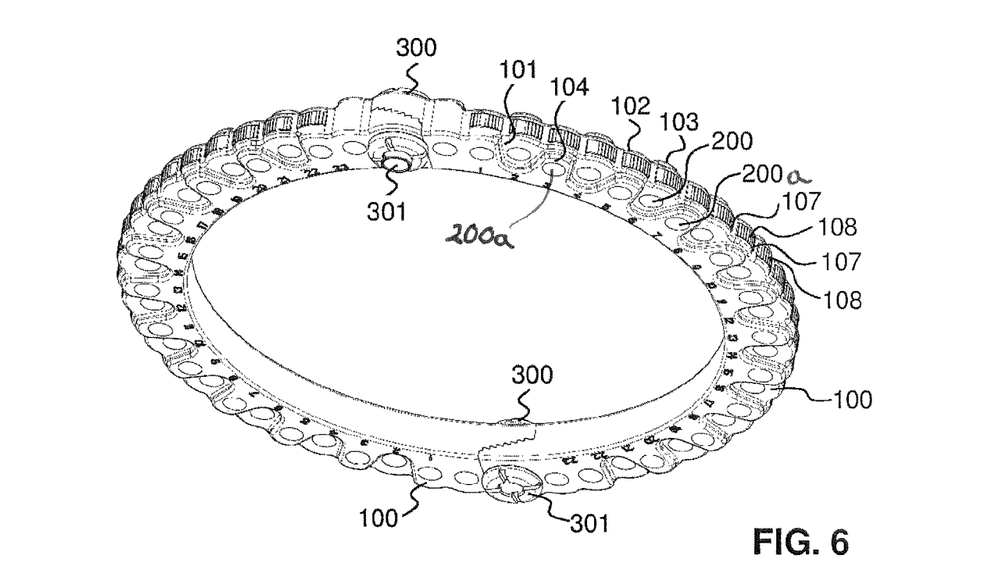
FIG. 6 shows a perspective view of third embodiment of an external fixation ring according to the present invention.
Figure 7:
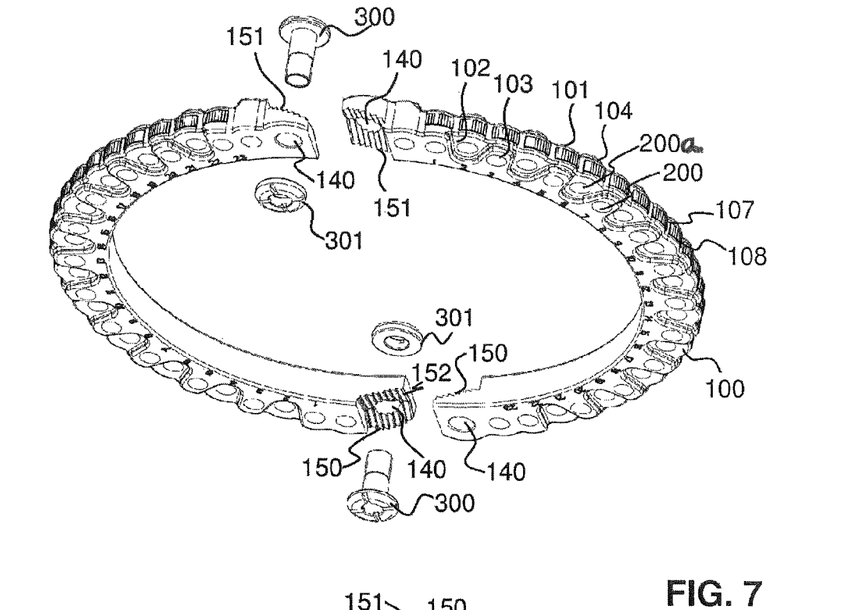
FIG. 7 shows a view of FIG. 6 in a disassembled condition.
Figure 8:
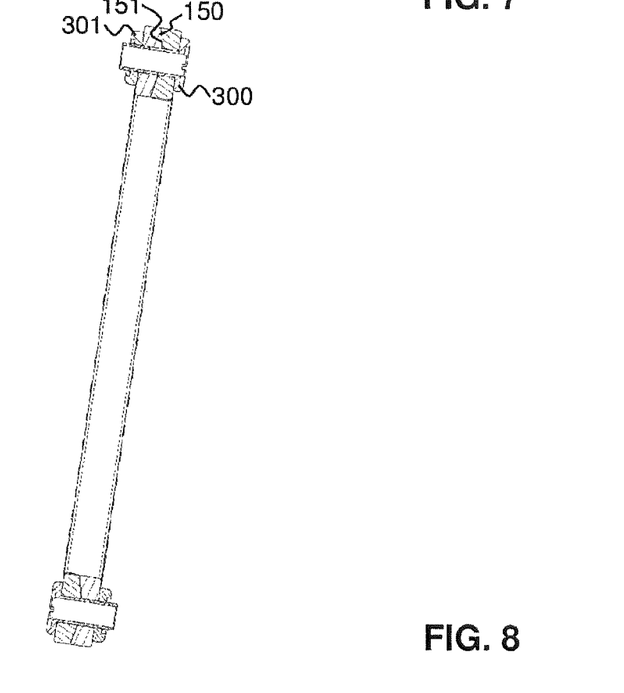
FIG. 8 shows a section view of FIG. 6 along lines 8-8 thereof.

Referring to FIGS. 6 to 8 there is shown a further embodiment of the present invention. Same parts are designated with the same reference numerals. The ring as shown in this embodiment is a closed ring that is provided by two ring halves which are joined together by means of two screws 300 and nuts 301 shown in FIG. 6.

Thereby each ring half comprises at each end one connection surface 150, 151 preferably being arranged at an angle to the first surface 101. The connection surfaces 150, 151 comprises a plurality of connection ribs 152 extending from the respective surface into the fixation plate 100. Thereby the connection ribs 152 of the first ring half are in engagement with the connection ribs 152 of the second ring half in order to provide a form closure between the two ring halves. A through opening 140 extends parallel to the centre axis M through the fixation plate 100 in the area of the connection surfaces 150, 151. The through opening 140 is arranged in order to accommodate a screw 300. Screw 300 is designed as a hollow screw having a through opening 302 extending along a central axis of the screw, however a solid screw may also be used. The opening 302 of the hollow screw preferably has the same diameter and serves the same function as an opening 200 to accommodate the same elements to fix a wire to the ring.

As it can be seen in the cross sectional view of FIG. 8 the form closure provided by the ribs 152 may be enhanced by providing the connection surfaces 150, 151 as angular or v-shaped surfaces. Thereby each connection surface 150, 151 comprises two sections which are oriented at an angle to each other.

Figure 9:
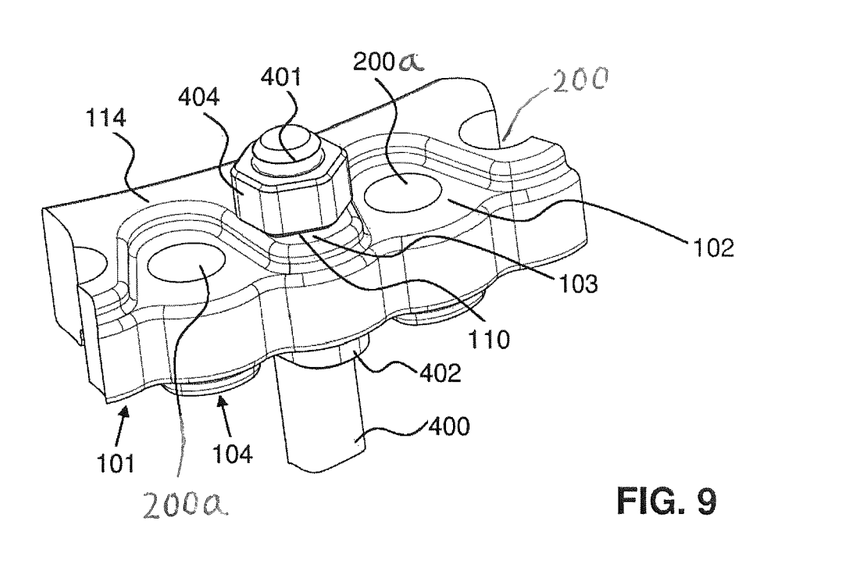
FIG. 9 shows a detailed view of an orthopedic fixation ring or plate according to the present invention.
Figure 10:
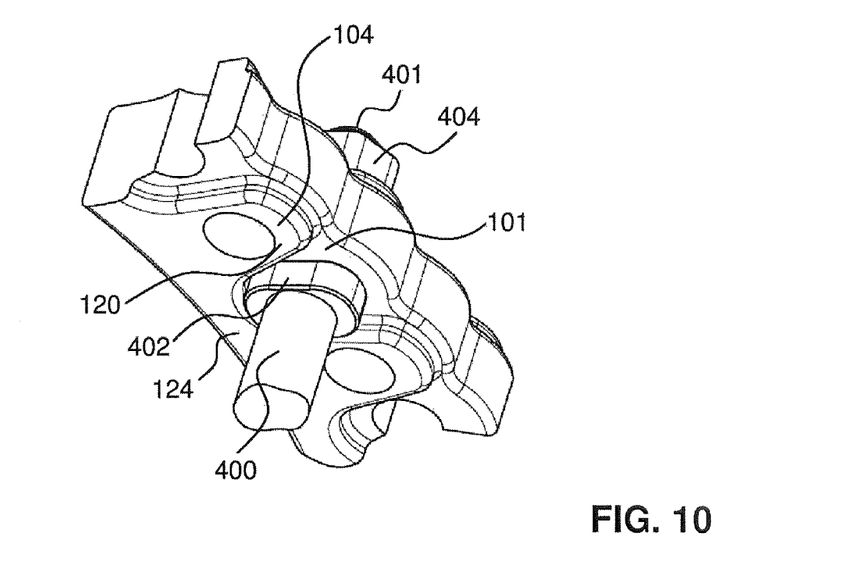
FIG. 10 shows a detailed view of an orthopedic fixation ring or plate according to the present invention.

FIGS. 9 and 10 show schematically that part of a clamping element or a wire post 400 to fixate a wire to a ring which extends through the opening 200. The wire post or clamping element 400 comprises a threaded portion 401, a flange portion 402 and a clamping portion 403. The flange portion 402 adjoins the threaded portion 401 and a clamping portion 403 adjoins the flange portion 402.

The threaded portion 401 is arranged to be in an engagement with a threaded nut 404. As it can be seen from the figures the threaded portion 401 extends through opening 200. Thereby the clamping element or wire post 400 is held by means of the flange portion 402 and the nut 404 in an axial fixed position in the opening 200.

From FIG. 10 it can be seen that the clamping element 400 is preferably arranged such that flange portion 402 is arranged between two embossments 120 such that a rotation around the axis of the clamping element 400 is prevented. Therefore the medical practitioner is able to tighten the nut 404 with one tool only as the counter-torque is compensated via the embossments 120 being in engagement with the flange portion 402.

The ring may be made out of fiber reinforced polymers such as carbon fiber reinforced PEEK. Alternately, it can be made out of metal such as stainless steel. The screw and nut are preferably metal such as stainless steel titanium or aluminium.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation system comprising:
a circular ring or part-circular ring segment extending around a central axis, the circular ring or part circular ring segment comprising a one-piece body having first and second outer surfaces each extending perpendicular to the central axis with a multiplicity of through openings extending therethrough, the first and second outer surfaces spaced from one another with respect to the central axis;
the one-piece body further comprising a multiplicity of first raised surfaces extending from the second surface and separated by valleys formed by the second outer surface, the first raised surfaces being integral with the second outer surface, each raised surface of the multiplicity of first raised surfaces surrounding a respective opening, wherein said first raised surfaces provide a third outer surface which is parallel to said first outer surface and said second outer surface wherein the third outer surface is spaced from the first outer surface and second outer surface with respect to the central axis.

2. The external fixation system according to claim 1, the one-piece body further comprising a multiplicity of second raised surfaces extending away from the first outer surface and separated by valleys formed by the first outer surface; and each second raised surface of the multiplicity of second raised surfaces surrounds a respective through opening, wherein said second raised surfaces provide a fourth outer surface.

3. The external fixation system according to claim 2, wherein said multiplicity of through openings are numbered with said first raised surfaces allocated to every even-numbered through opening of the multiplicity of through openings and wherein said even-numbered through openings extend from the first outer surface to the third outer surface;
wherein second raised surfaces are allocated to every odd-numbered through openings of the multiplicity of through openings and wherein every odd-numbered through opening extends from the second outer surface to the fourth outer surface.

4. The external fixation system according to claim 2, wherein said first raised surfaces are spaced apart at regular intervals over the second outer surface and the second raised surfaces are spaced apart at regular intervals distributed over the first outer surface.

5. The external fixation system according to claim 2, wherein each second raised surface is separated by a portion of the first outer surface and are connected by means of a portion of the fourth ring surface with a neighboring second raised surface.

6. The external fixation system according to claim 1, wherein said multiplicity of through openings are even and odd numbered wherein each even-numbered through opening extends through the first raised surface from the first outer surface to the third outer surface and wherein every odd-numbered through opening extends from the first outer surface to the second outer surface.

7. The external fixation system according to claim 1, wherein edges of the first raised surfaces are tapered towards said through openings such that a clearance between two neighboring first raised surfaces decreases towards the through openings and increases away from the through openings as viewed in a radial direction from a ring central axis.

8. The external fixation system according to claim 1, wherein a first raised surface is connected by means of a web with a neighboring first raised surface.

9. The external fixation system according to claim 1, wherein two ring segments are connected by means of screws.

10. The external fixation system according to claim 9, wherein each screw has an axial bore along a middle axis of the screw.

11. The external fixation system according to claim 9, wherein each end of said ring segments comprises a connection portion having a surface which extends at an angle to the first surface.

12. The external fixation system according to claim 11, wherein an opening extends through said connection portion which opening is adapted to receive said screw.

13. The external fixation system according to claim 12, wherein the connection portion surface comprises a plurality of connection ribs extending from each connection portion angled surface.

14. An external fixation system comprising a support ring or a ring segment, each ring or ring segment comprising a one-piece body extending around a ring or ring segment central axis, the ring or ring segment one-piece body comprising a first outer surface extending perpendicular to the central axis, a second outer surface which is parallel to the first outer surface, a plurality of spaced apart through openings running parallel to the central axis, a first group of through openings extending through the support ring or ring segment from the first outer surface to the second outer surface; and a third outer surface which is parallel to the first and second outer surfaces with a second group of through openings running parallel to said central axis extending from the first outer surface to the third outer surface and wherein the first, second and third outer surfaces are axially spaced apart with respect to the central axis from each other, wherein the third outer surface is formed by a plurality of circumferentially spaced first raised surfaces integrally formed on the second outer surface, the first raised surfaces separated by valleys formed by the second outer surface, and wherein the first raised surfaces are spaced around the support ring or ring segment by the valleys formed by the second outer surface such that the first and second groups of through openings alternate around the ring or ring segment.

15. The external fixation system according to claim 14, wherein the first raised surfaces are connected by means of a portion of the second outer surface with neighboring first raised surfaces.

16. The orthopaedic fixation ring according to claim 14, wherein edges of the first raised surfaces are tapered towards said through openings such that a clearance between two neighboring first raised surfaces decreases towards the openings and increases away from the openings as viewed in a radial direction from the central axis.

* * * * *